US008771306B2

(12) United States Patent
Fischvogt et al.

(10) Patent No.: US 8,771,306 B2
(45) Date of Patent: Jul. 8, 2014

(54) INSERTION DEVICE AND METHOD OF USE

(75) Inventors: Gregory Fischvogt, Hamden, CT (US); Tia Ferrarotti, Milford, CT (US)

(73) Assignee: Covidien LP, Mansfield, MA (US)

( * ) Notice: Subject to any disclaimer, the term of this patent is extended or adjusted under 35 U.S.C. 154(b) by 607 days.

(21) Appl. No.: 13/020,825

(22) Filed: Feb. 4, 2011

(65) Prior Publication Data

US 2011/0224679 A1    Sep. 15, 2011

Related U.S. Application Data

(60) Provisional application No. 61/312,748, filed on Mar. 11, 2010.

(51) Int. Cl.
*A61B 17/34* (2006.01)
(52) U.S. Cl.
USPC ............................................. 606/185
(58) Field of Classification Search
USPC .................... 606/167, 170, 181–183, 185
See application file for complete search history.

(56) References Cited

U.S. PATENT DOCUMENTS

| | | | | |
|---|---|---|---|---|
| 2,655,154 | A | * | 10/1953 | Richter .......................... 606/159 |
| 4,519,100 | A | | 5/1985 | Wills et al. |
| 4,729,374 | A | | 3/1988 | Alfranca |
| 4,963,147 | A | | 10/1990 | Agee et al. |
| 5,053,044 | A | | 10/1991 | Mueller et al. |
| 5,443,475 | A | | 8/1995 | Auerbach et al. |
| 5,586,990 | A | | 12/1996 | Hahnen et al. |
| 5,624,459 | A | * | 4/1997 | Kortenbach et al. .......... 606/185 |
| 7,056,329 | B2 | | 6/2006 | Kerr |
| 2004/0093001 | A1 | | 5/2004 | Hamada |
| 2007/0167968 | A1 | | 7/2007 | Pandey |
| 2007/0225740 | A1 | | 9/2007 | Suddaby |
| 2008/0045989 | A1 | | 2/2008 | Welborn |

FOREIGN PATENT DOCUMENTS

| | | | |
|---|---|---|---|
| WO | WO 2006/083679 | | 8/2006 |
| WO | WO 2008103308 A1 | * | 8/2008 ............. A61B 17/34 |

OTHER PUBLICATIONS

European Search Report for corresponding EP11250282 date of mailing is Jun. 18, 2011 (3 pages).

* cited by examiner

*Primary Examiner* — Ashley Fishback

(57) ABSTRACT

An insertion device for safely creating an incision through tissue is provided. The device includes a tubular member and a cutting assembly. The tubular member includes proximal and distal ends and defines a passageway therethrough. The tubular member includes at least one longitudinal slot extending proximally from a distal end thereof. The cutting assembly includes a blade assembly mounted on a distal end thereof. The distal end of the cutting assembly is configured for sliding reception within the passageway of the tubular member. The blade assembly includes at least one blade movable between a retracted position and an extended position. The blade assembly is configured such that the at least one blade is received through the at least one longitudinal slot of the tubular member when the at least one blade is in an extended position.

5 Claims, 7 Drawing Sheets

INSERTION DEVICE AND METHOD OF USE

CROSS REFERENCE TO RELATED APPLICATION

The present application claims the benefit of and priority to U.S. Provisional Application Ser. No. 61/312,748 filed on Mar. 11, 2010, the entire contents of which are incorporated herein by reference.

BACKGROUND

1. Technical Field

The present disclosure relates to devices for accessing the abdominal cavity. More particularly, the present disclosure relates to apparatuses and methods for safely inserting an access assembly into an abdominal cavity.

2. Background of Related Art

Assemblies configured for accessing a body cavity are known. Many of such access assemblies include a rigid cannula or sleeve that is inserted through an incision created by a surgeon in the tissue of a patient. The incision into the abdominal cavity may be created by the surgeon using a scalpel or other bladed instrument. Alternatively, the cannula may include a piercing tip, i.e., a blade or pointed distal end. Creating an incision through skin into the abdominal cavity using a scalpel risks damaging underlying internal organs. Creating an incision using a scalpel may also result in plane shifting of the tissue layers around the incision. Plane shifting of the tissue makes inserting of a non-cutting cannula through the incision more difficult. Although using a piercing cannula eliminates the possibility of tissue plane shifting, forcing a cannula through the abdominal wall and into the abdominal cavity may result in puncturing of internal organs and other peripheral tissue damage.

Therefore, it would be beneficial to have a device and method for safely inserting an access device through the tissue and into the abdominal cavity of a patient.

SUMMARY

An insertion device for safely creating an incision through tissue is provided. The device includes a tubular member and a cutting assembly. The tubular member includes proximal and distal ends and defines a passageway therethrough. The tubular member includes at least one longitudinal slot extending proximally from a distal end thereof. The cutting assembly includes a blade assembly mounted on a distal end thereof. The distal end of the cutting assembly is configured for sliding reception within the passageway of the tubular member. The blade assembly includes at least one blade movable between a retracted position and an extended position. The blade assembly is configured such that the at least one blade is received through the at least one longitudinal slot of the tubular member when the at least one blade is in an extended position.

In one embodiment, the proximal end of the tubular member is configured to facilitate engagement by a user. The proximal end of the tubular member may include a handle. The blade assembly may include two blades. In another embodiment, at least one blade is biased to an extended position. A proximal end of the cutting assembly may be configured to facilitate engagement by a user. A cutting surface of the at least one blade may face proximally when the at least one blade is in an extended position. The tubular member may be configured to receive an access device thereabout. The cutting assembly may include a handle configured to move the at least one blade between the extended and retracted positions. The distal end of the tubular member may include a piercing tip. The at least one blade may be configured to pierce tissue when in the retracted position. The longitudinal slot may extend substantially along a length thereof.

Also provided is a method of creating an incision in tissue. The method includes the step of providing an insertion device having a tubular member and a cutting assembly, wherein the tubular member includes at least one longitudinal slot extending proximally from a distal end thereof and is configured to be received through tissue, wherein a blade assembly of the cutting assembly is configured to be slidingly received through the longitudinal slot of the tubular member. The method further includes the steps of inserting a distal end of the tubular member through tissue of a patient and into a body cavity, inserting the cutting assembly through the tubular member such that the at least one blade of the blade assembly is received within the longitudinal slot of the tubular member, retracting the cutting assembly relative to the tubular member to create an incision about the tubular member.

The method may further include the steps of inserting an access port through the tissue about the tubular member and removing the tubular member from within the access port. The method may also include the steps of moving the at least one blade from a retracted position to an extended position and retracting the cutting assembly from within the tubular member. The method may additionally include the step of removing the access port from within the tissue and closing the incision.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

Figure 1:
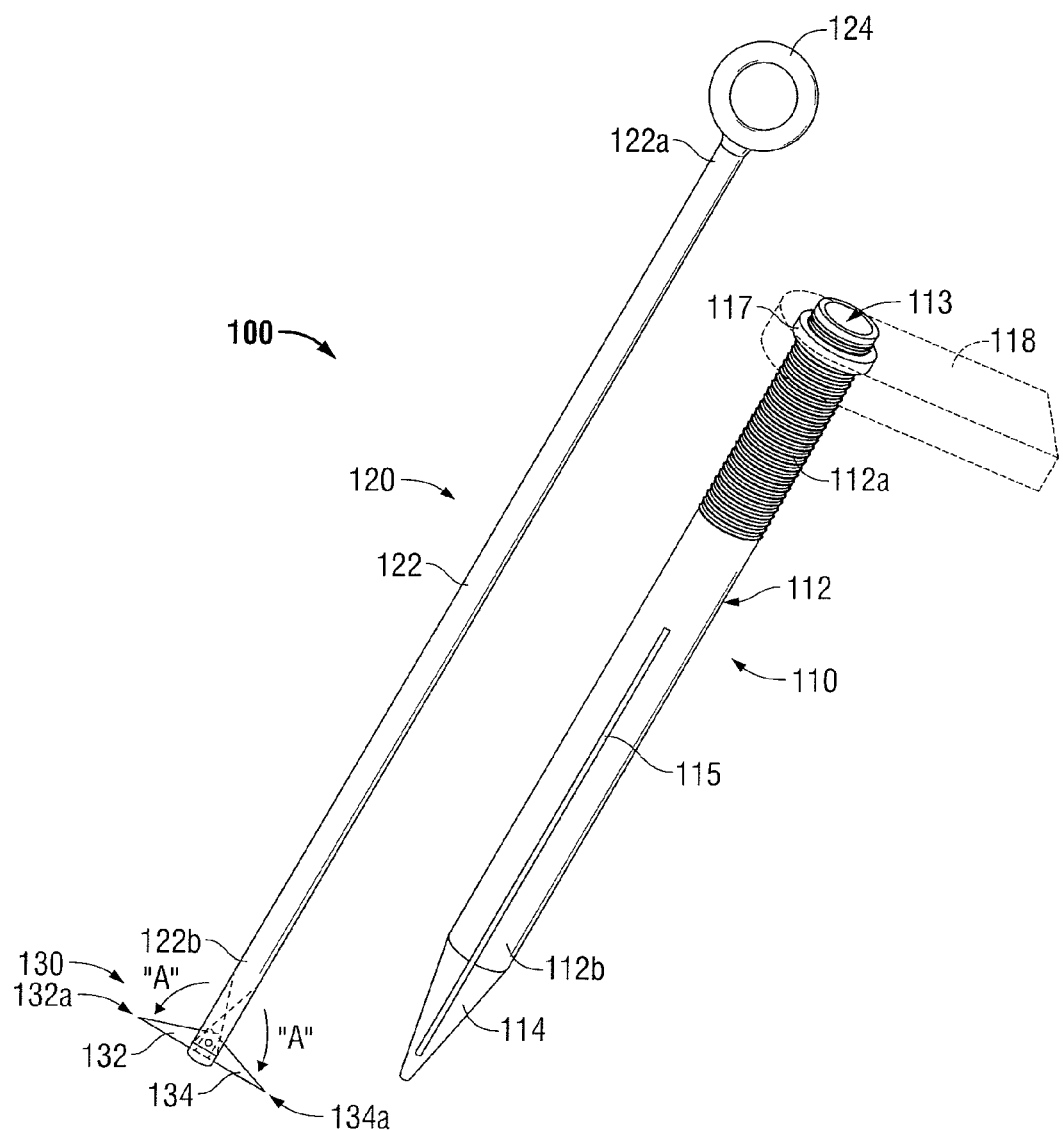
FIG. 1 is as a separated perspective view of an embodiment of an insertion device according to the present disclosure.
Figure 2:
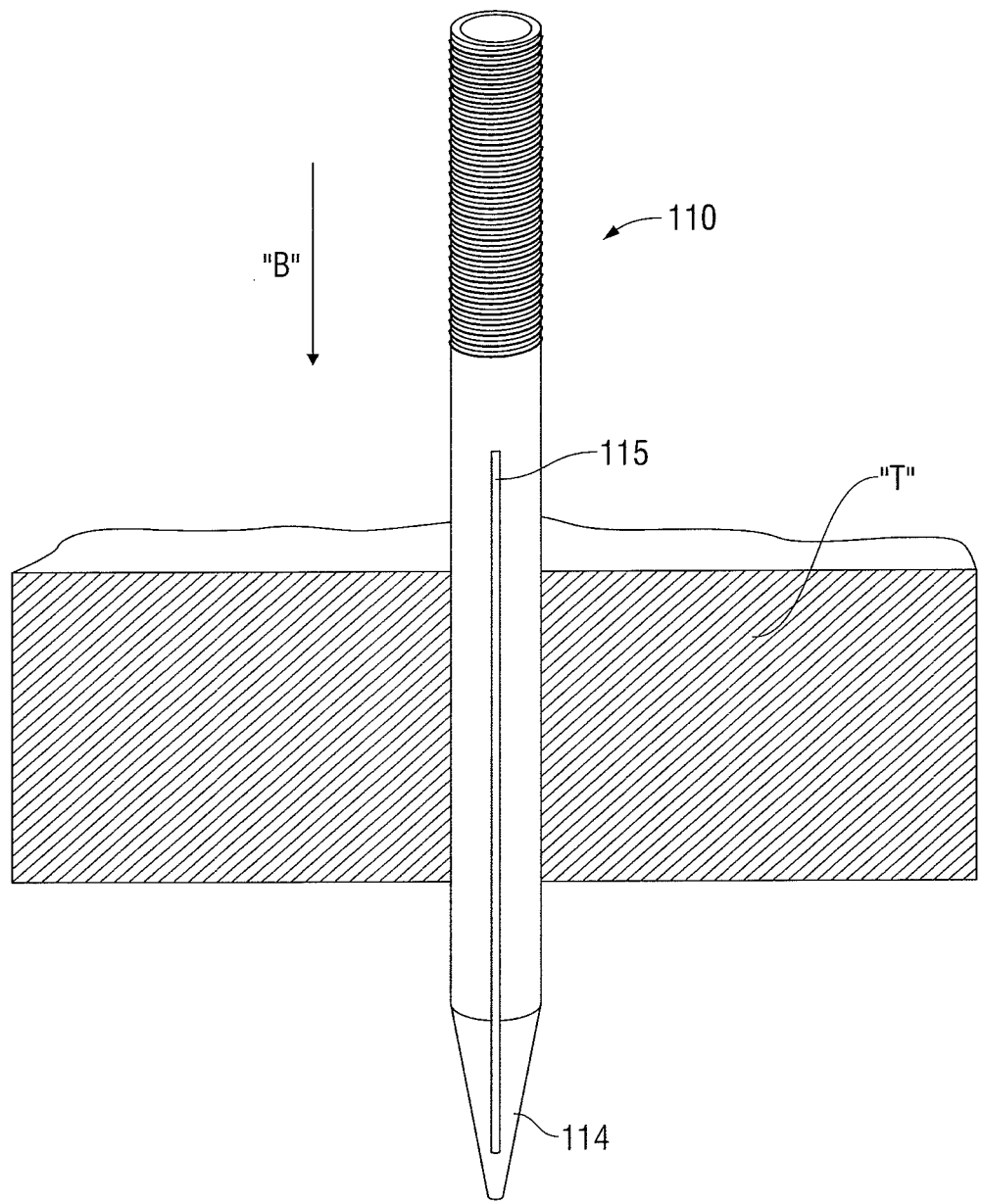
FIG. 2 is a side view of the sleeve of the insertion device of FIG. 1 received through tissue.

With reference to FIG. 1, an apparatus for safely inserting an access assembly into an abdominal cavity of a patient is shown generally as insertion device 100. Insertion device 100 includes a sleeve or cannula 110 and a cutting assembly 120.

It is envisioned that sleeve 110 and cutting assembly 120 may be separable, as shown, or cutting assembly 120 may be operably secured within sleeve 110. Either or both of sleeve 110 and cutting assembly 120 may be disposable or sterilizable for reuse.

Still referring to FIG. 1, sleeve 110 defines a tubular member 112 having proximal and distal ends 112a, 112b and defining a passageway 113 therebetween. Although shown having a substantially cylindrical cross-section, tubular member 112 may include alternative cross-sectional configurations, including rectangular, oval and triangular. Tubular member 112 may be constructed of metal, plastic or other suitable material. Tubular member 112 may be transparent, translucent or otherwise configure for viewing cutting assembly 120 therethrough. As will be discussed in further detail below, passage 113 is configured to receive at least a distal end 122b of cutting assembly 120 in a sliding manner. In one embodiment, tubular member 112 is substantially similar in size to a large needle, i.e. Veress® needle. In this manner, member 112 may be received through the tissue of a patient with minimal force and with minimal risk of damaging internal organs. As will be discussed in further detail below, tubular member 112 is also slim enough to be received through a cannula 52 (FIG. 5) of an access assembly 50. Tubular member 112 is of a sufficient length to be received through the tissue of the abdominal wall of a patient and to extend through access assembly 50 when access assembly 50 is received thereabout.

With reference still to FIG. 1, proximal end 112a of tubular member 112 includes a flange 117 thereabout. Flange 117 may facilitate engagement of tubular member 112 by a surgeon. Alternatively, flange 117 may be configured for selective engagement within a handle member 118 (shown in phantom). As will be discussed in further detail below, flange 117 is sized to be received with cannula 52 of an access assembly 50. Proximal end 112a may instead or may also include knurling, ridges or other suitable configuration to facilitate engagement by a clinician during use. Proximal end 112a of tubular member 112 may instead, or additionally include a handle. Proximal end 112a may include a tapered outer surface to facilitate reception of access assembly "A" thereover during insertion of access assembly "A" into the abdominal cavity of the patient. Proximal end 112a may also include a tapered inner surface for facilitating reception of cutting assembly 120 therethrough.

Still referring to FIG. 1, distal end 112b of tubular member 112 includes a piercing tip 114. As shown, piercing tip 114 is integrally formed with tubular member 112; however, it is envisioned that that piercing tip 114 may be removably or fixedly secured with tubular member 112. Piercing tip 114 may be conical, as shown, or include one or more blade members. Distal end 112b of tubular member 112 defines a longitudinal slot 115 extending across and proximally along a length thereof. Longitudinal slot 115 may extend through piercing tip 114. Longitudinal slot 115 extends proximally along tubular member 112 to a point distal of proximal end 112a. Tubular member 112 is configured such that a proximal end of longitudinal slot 115 extends beyond tissue "T" after tubular member 112 has been received through tissue "T" of a patient. As will be discussed in further detail below, longitudinal slot 115 is configured to slidingly receive of a pair of cutting blades 132 of cutting assembly 120 as cutting assembly 120 is withdrawn through passage 113.

With reference still to FIG. 1, cutting assembly 120 includes an elongated shaft 122 having proximal and distal ends 122a, 122b. A handle member 124 is mounted on proximal end 122a of elongated shaft 122 and a blade assembly 130 is operably mounted on distal end 122b thereof. As shown, handle member 124 is integrally formed with elongated shaft 122; however, handle member 124 may be removably or fixedly secured with elongated shaft 122. When integrally formed with or fixedly secured to elongated shaft 122, and therefore, not removable, handle member 124 must be small enough to be received through the cannula of the access assembly being used to access the abdominal cavity. Handle member 124 is configured to facilitate engagement of cutting assembly 120 by a user during reciprocation of cutting assembly 120 within sleeve 110.

Still referring to FIG. 1, blade assembly 130 includes a pair of blade members 132, 134. Although shown including a pair of blades, it is envisioned that blade assembly 130 may include only a single blade or may include three or more blades. Blade members 132, 134 each include a linear cutting surface 132a, 134a. Blades 132, 134 are pivotably secured to distal end 122b of elongated shaft 122. In a first or retracted position, blades 132, 134 (shown in phantom) are turned upwards to permit reception through tubular member 112. In a second or extended position, blades 132, 134 are pivoted outwardly, as indicated by arrows "A". In the extended position, cutting surfaces 132a, 134a of blades 132, 134, respectively, are oriented in a proximal direction. Blades 132, 134 may be spring loaded to bias blades 132, 134 into the second position once completely received through tissue "T". Alternatively, blades 132, 134 may be weighted and/or otherwise configured to pivot outwardly to the extended position once distal end 122b of cutting assembly 120 has been completely received through tissue "T".

Figure 3:
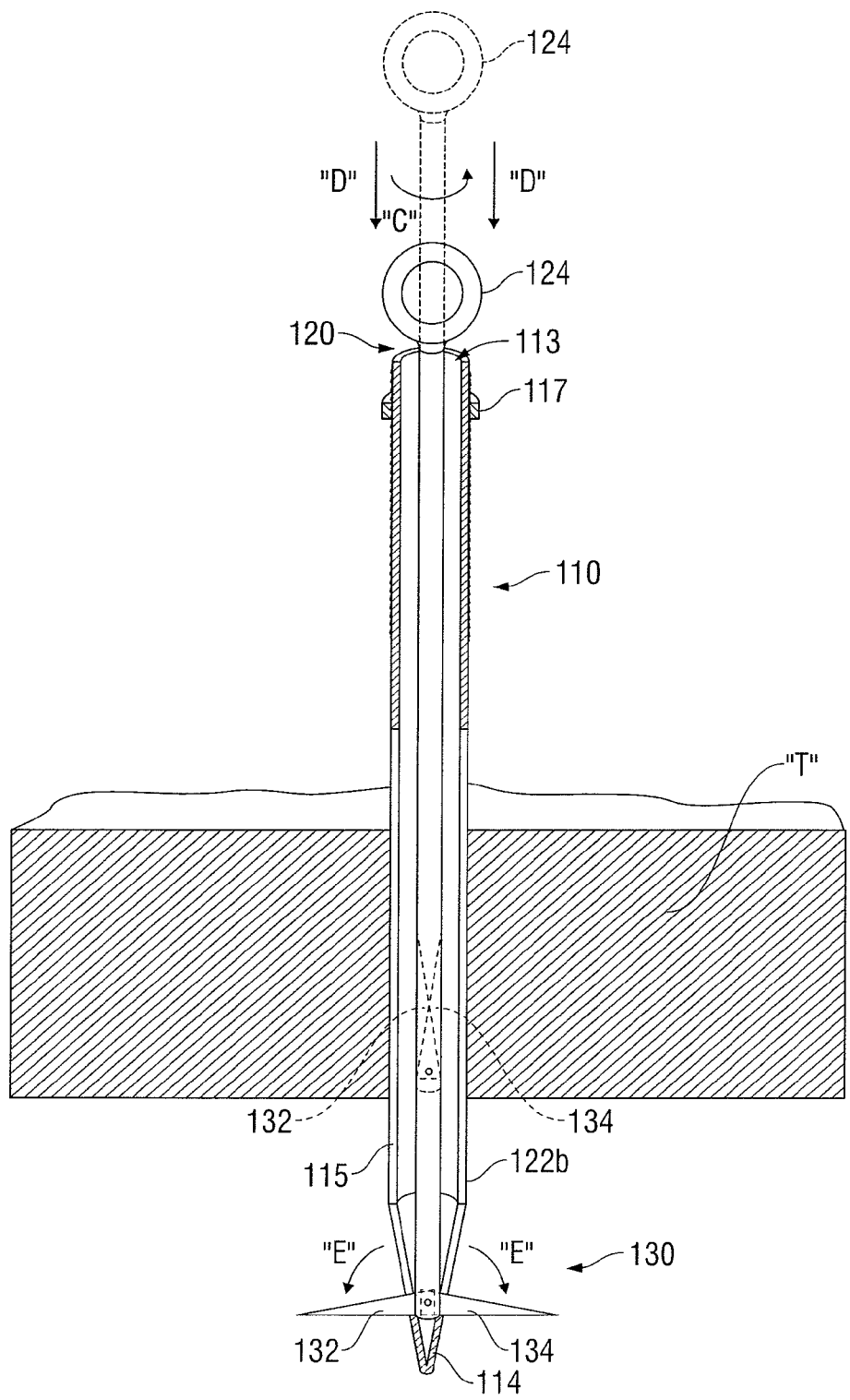
FIG. 3 is a side view of the insertion device of FIG. 1 with the cutting assembly shown at various stages of insertion through the sleeve.

The use of insertion assembly 100 will not be described with reference to FIGS. 2-5. Initially, sleeve 110 is inserted through tissue "T", as indicated by arrow "B", such that piercing tip 114 of sleeve 110 is received within the abdominal cavity of a patient and a sufficient portion of longitudinal slot 115 is exposed to permit extension of blades 132, 134 when distal end 122b of cutting assembly 120 is received through sleeve 110 (FIG. 3). Cutting assembly 120 may be received within sleeve 110 during insertion of sleeve 110 through tissue "T". Alternatively, and as shown, cutting assembly 120 is inserted into sleeve 110 once sleeve 110 has been properly positioned through tissue "T".

With reference now to FIG. 3, to be received within passageway 113 of sleeve 110, blade assembly 130 of cutting assembly 120 must be in a first or retracted position (shown in phantom). As discussed above, proximal end 112a of sleeve 110 may include a tapered inner surface to facilitate reception of distal end 122b of cutting assembly 120 therein. To prevent blades 132, 134 from prematurely extending to the second position, cutting assembly 120 may be rotated along its longitudinal axis, as indicated by arrow "C", within passageway 113 sufficiently such that blades 132, 134 are misaligned with longitudinal slot 115. In this manner, a clinician would be required to rotate cutting assembly 120 back to its initial orientation to align blades 132, 134 of blade assembly 130 with longitudinal slot 115 for proper deployment of blades 132, 134. Cutting assembly 120 is received through sleeve 110, as indicated by arrows "D". Once blades 132, 134 of blade assembly 130 clear tissue "T" and are aligned with longitudinal slot 115, blades 132, 134 move from the first or retracted position to the second or extended position, as indicated by arrows "E", wherein the blades 132, 134 are disposed transverse to the tubular member 112.

Figure 4:
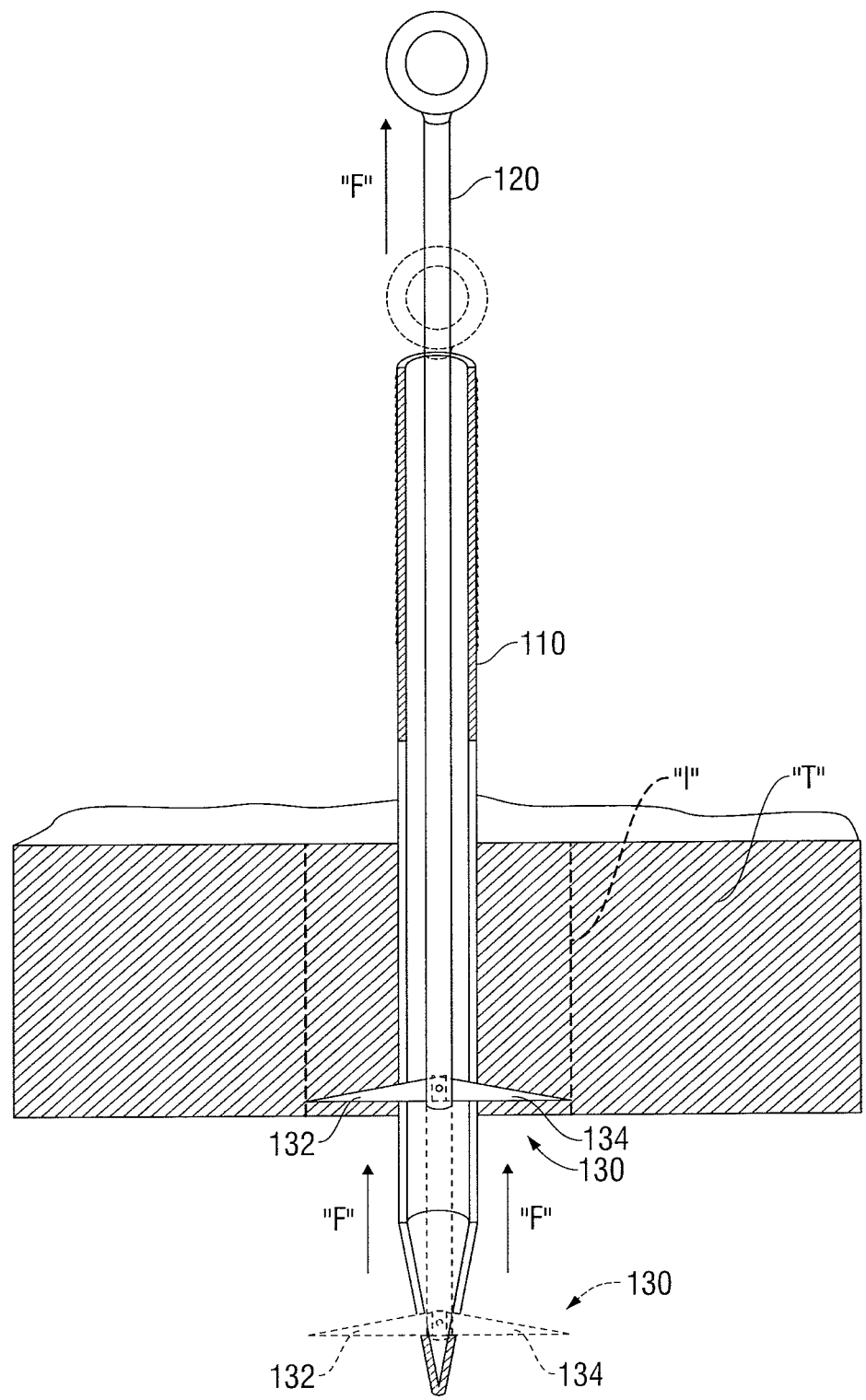
FIG. 4 is a side view of the insertion device of FIG. 1 with the cutting assembly shown at various stages of withdrawal from the sleeve.

With reference now to FIG. 4, retraction of cutting assembly 120 relative to sleeve 110, as indicated by arrows "F", causes engagement of blade assembly 130 with tissue "T". Cutting assembly 120 is then retracted through sleeve 110 until blades 132, 134 of blade assembly 130 completely cut through tissue "T". Cutting assembly 120 may then be removed from sleeve 110 (not shown), or, as discussed above, cutting assembly 120 may remain secured within sleeve 110. If removable handle 118 (FIG. 1) has been used to facilitate operation of insertion device 100, handle 118 is disengaged from flange 117 (FIG. 1) and is removed from sleeve 110 to permit the passage of cannula 52 thereover.

Figure 5:
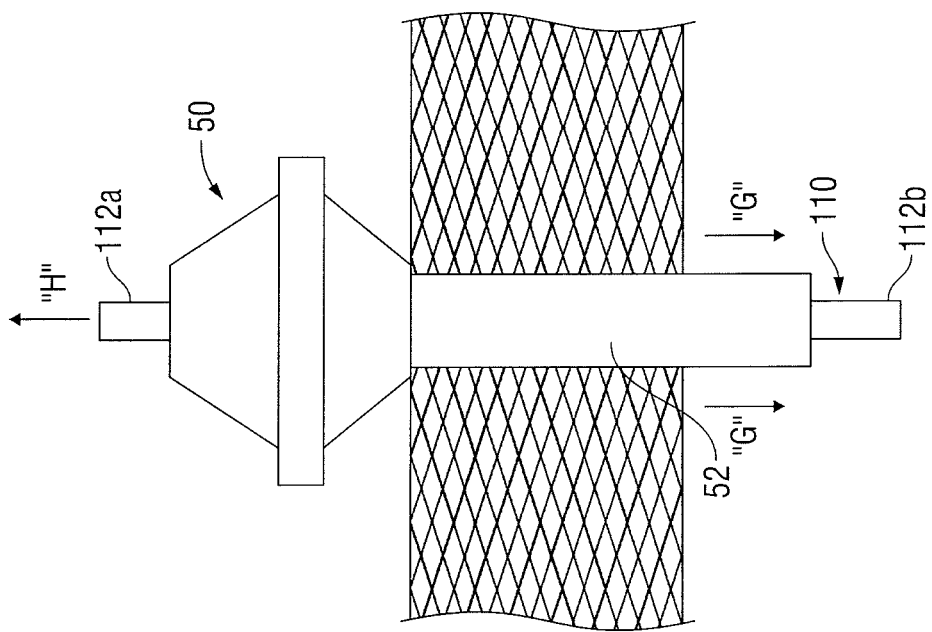
FIG. 5 is a side view of an access assembly received about the sleeve of the cutting assembly of FIG. 1 and through tissue.

Turning now to FIG. 5, cannula 52 of an access assembly 50 is received about proximal end 112a of sleeve 110 and is inserted through incision "I" created in tissue "T", as indicated by arrows "G". Cannula 52 may have a tapered distal end (not shown) to facilitate reception through tissue "T". As discussed above, cannula 52 of access assembly 50 may also be received about cutting assembly 120. Once cannula 52 has been received through tissue "T", sleeve 120 is removed from within access assembly 50, in the direction indicated by arrow "H".

Figure 6:
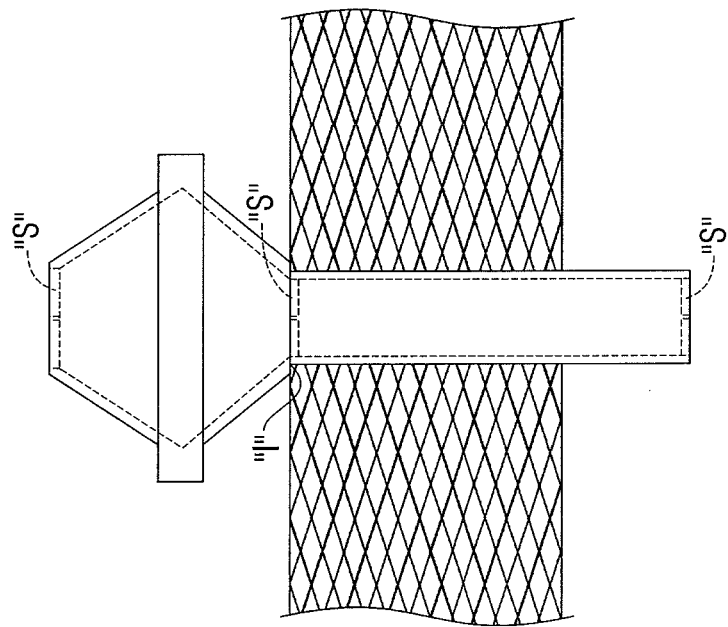
FIG. 6 is a side view of the access assembly of FIG. 5 received through tissue.

With reference now to FIG. 6, access assembly 50 may then be used in a conventional manner. Access assembly 50 may include one or more seals "S" configured for receiving instruments therethrough in a sealing manner. Although shown used for inserting access assembly 50, it is envisioned that the devices and methods of the present disclosure may be used for inserting access assemblies of alternate sizes and configurations. Upon completion of a procedure, access assembly 50 is removed from tissue "T" and incision "I" is closed in a conventional manner.

Although shown and described as making a single pass through tissue "T", thereby creating a single incision "I", it is envisioned that cutting assembly 120 of insertion device 100 may be passed through tissue "T" multiple times to make multiple incisions. When used to make multiple incisions in tissue "T", cutting assembly 120 is reinserted through sleeve 110 in the manner described above. Then, either cutting assembly 120 or cutting assembly 120 and sleeve 110 are rotated along a longitudinal axis thereof to reoriented blades 132, 134 of blade assembly 130 relative to tissue "T" and initial incision "I". Cutting assembly 120 is then retracted in the manner described above. This process may be repeated one or more times to create one or more additional incisions through tissue "T", thereby easing the force required for the insertion of cannula "C" about sleeve 110 and through tissue "T".

Figure 7:
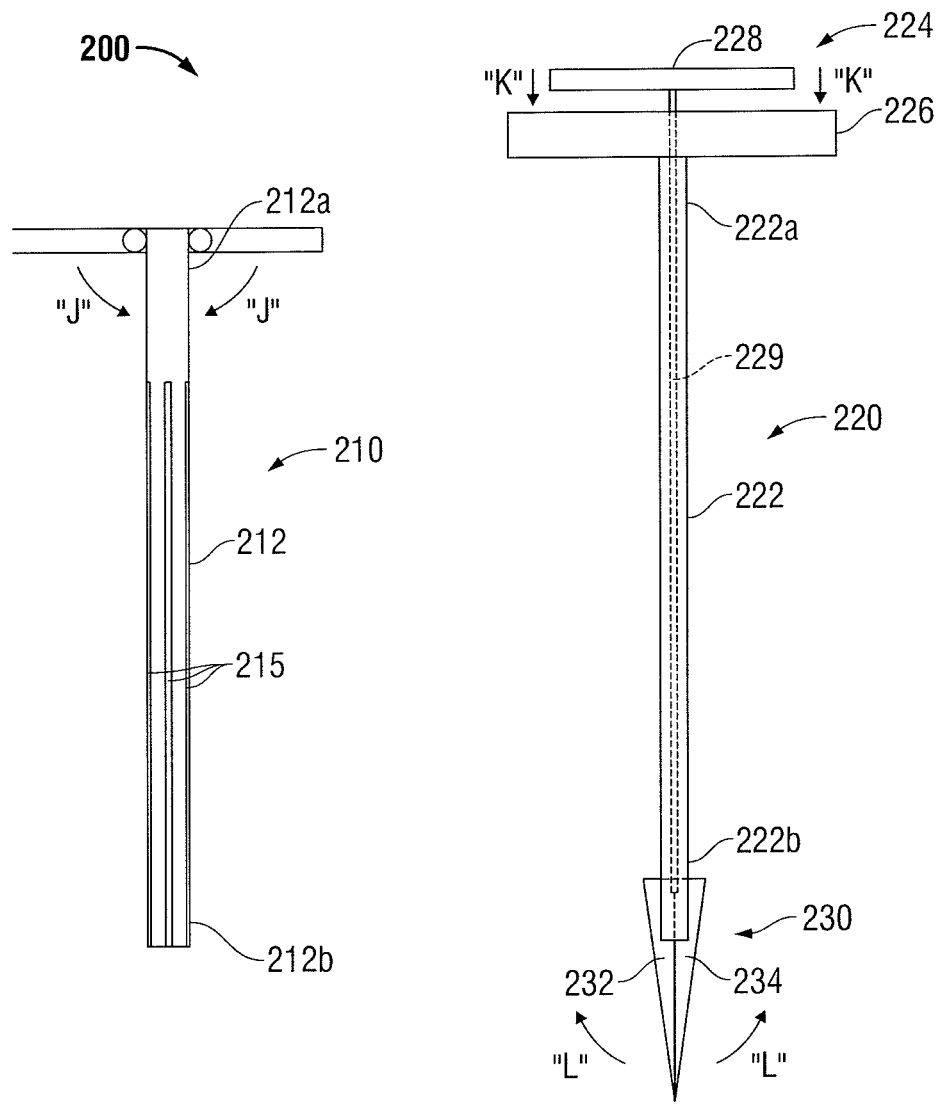
FIG. 7 is a separated side view of an alternative embodiment of an insertion device according to the present disclosure with the blade assembly of the cutting assembly in a first or retracted position.
Figure 8:
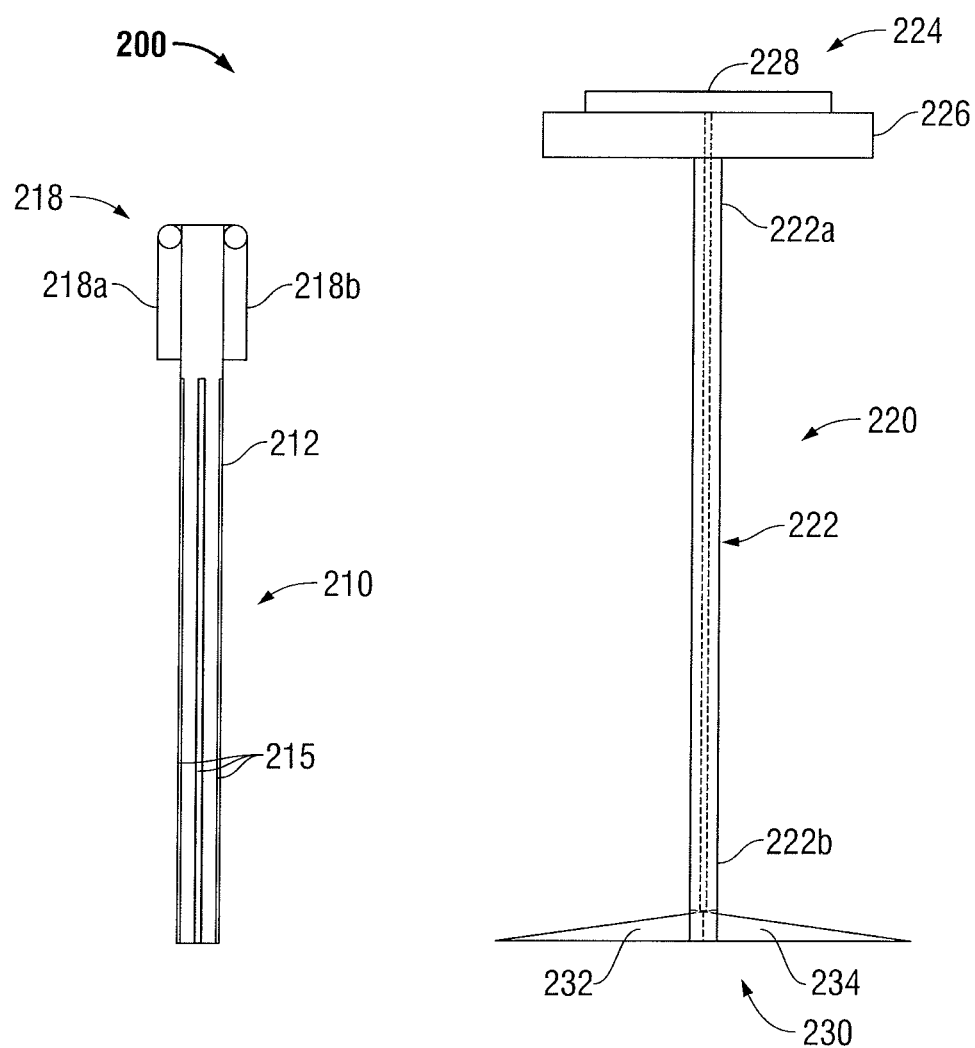
FIG. 8 is a separated side view of the insertion device of FIG. 7 with the blade assembly in a second or deployed position.

With reference now to FIGS. 7 and 8, an alternative embodiment of an insertion device according to the present disclosure is shown generally as insertion device 200. Insertion device 200 is substantially similar to insertion device 100 described hereinabove and will only be described as relates to the differences therebetween. Insertion device 200 includes a sleeve 210 and a cutting assembly 220.

With reference still to FIGS. 7 and 8, sleeve 210 of insertion device 200 defines a tubular member 212 having proximal and distal ends 212a, 212b and defining a passageway (not shown) therebetween. Proximal end 212a of tubular member 212 includes handle assembly 218. Handle assembly 218 includes a pair of handle member 218a, 218b that are pivotably connected to proximal end 212a of tubular member 212. Handle members 218a, 218b are configured to facilitate engagement of tubular member 212 by a user. Handle members 218a, 218b are configured to pivot, in the direction indicated by arrows "J", towards tubular member 212 to reduce the profile handle assembly 218, thereby permitting the passage of cannula 52 of access assembly 50 thereabout. is removable to permit an access assembly to be received about tubular member 212. Distal end 212b of tubular member 212 includes a plurality of longitudinal slots 215 formed along a length thereof.

Still referring to FIGS. 7 and 8, cannula assembly 220 includes an elongated shaft 222 having proximal and distal ends 222a, 222b. Elongated shaft 222 includes a handle assembly 224 operably mounted on proximal end 222a thereof and a blade assembly 230 operably mounted on distal end 222b thereof. Handle assembly 224 includes a fixed handle 226 and a movable handle 228. Movable handle 228 is operably connected to blades 232, 234 of blade assembly 230 and is configured to move blades 232, 234 between retracted (FIG. 7) and extended positions (FIG. 8). An activation shaft 229 extends the length of elongated shaft 222 and operably connects movable handle 228 with blade assembly 230. Movement of movable handle 228 towards fixed handle 226, in the direction indicated by arrows "K", causes blades 232, 234 of blade assembly 230 to pivot upwards, in the direction indicated by arrows "L", into a extended or deployed position. It is envisioned that in alternate embodiments, blades 232, 234 may be spring loaded in one of the retracted or extended positions and operation of moveable handle 228 causes the respective extension or retraction of blades 232, 234.

With continued reference to FIG. 7, in the retracted position, blades 232, 234 of blade assembly 230 extend outwardly along elongated shaft 222. In this retracted position, blade assembly 230 is configured to pierce tissue "T". As such, when in the retracted position, blade assembly 230 may be used to pierce tissue "T" during insertion of sleeve 210 through tissue "T". In this manner, tubular member 212 may have a blunt or atraumatic distal end 212b.

With reference still to FIGS. 7 and 8, insertion device 200 operates in a manner similar to insertion device 100 described hereinabove and will only be described as relates to the differences therebetween. As discussed above, when received through sleeve 210, blade assembly 230 may be used to pierce tissue "T". Upon complete reception of sleeve 210 and distal end 222b of cutting assembly 220 through tissue "T", moveable handle 228 is approximated towards fixed handle 226 to move blades 232, 234 from the retracted position (FIG. 7) to the extended position (FIG. 8). Once blade assembly 230 has been completely received through tissue "T", moveable handle 228 may be approximated away from fixed handle 226 to cause the retraction of blades 232, 234 and permit the withdrawal of cutting assembly 220 from sleeve 210.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure. For example, the cutting assembly may have a removable or collapsible handle to facilitate reception of an access assembly thereover and thereabout.

What is claimed is:

1. A method of creating an incision in tissue, the method including:
    providing an insertion device having a tubular member and a cutting assembly, wherein the tubular member includes at least one longitudinal slot extending proximally from a distal end thereof and is configured to be received through tissue, wherein a blade assembly of the cutting assembly is configured to be slidingly received through the longitudinal slot of the tubular member;

inserting the distal end of the tubular member through tissue and into a body cavity;

inserting the cutting assembly through the tubular member;

moving at least one blade of the blade assembly from a retracted position in which a linear cutting surface of the at least one blade is disposed along the tubular member to an extended position in which the linear cutting surface of the at least one blade is disposed transverse to the tubular member such that the at least one blade of the blade assembly is received through the longitudinal slot of the tubular member; and retracting the cutting assembly relative to the tubular member to create an incision about the tubular member.

2. The method of claim 1, further including inserting an access port through the tissue about the tubular member.

3. The method of claim 2, further including removing the tubular member from within the access port.

4. The method of claim 2, further including removing the access port from within the tissue and closing the incision.

5. The method of claim 1, further including retracting the cutting assembly from within the tubular member.

\* \* \* \* \*